United States Patent
Sakurai et al.

(10) Patent No.: US 9,594,069 B2
(45) Date of Patent: Mar. 14, 2017

(54) TEXTURE INDICATION MEASURING METHOD AND MEASURING DEVICES

(75) Inventors: Naoki Sakurai, Hiroshima (JP); Shinichiro Iwatani, Hiroshima (JP); Hidemi Akimoto, Hiroshima (JP)

(73) Assignee: HIROSHIMA UNIVERSITY, Hiroshima (JP)

(*) Notice: Subject to any disclaimer, the term of this patent is extended or adjusted under 35 U.S.C. 154(b) by 936 days.

(21) Appl. No.: 13/820,050

(22) PCT Filed: Aug. 31, 2011

(86) PCT No.: PCT/JP2011/069851
§ 371 (c)(1),
(2), (4) Date: May 10, 2013

(87) PCT Pub. No.: WO2012/029888
PCT Pub. Date: Mar. 8, 2012

(65) Prior Publication Data
US 2013/0228016 A1    Sep. 5, 2013

(30) Foreign Application Priority Data
Aug. 31, 2010  (JP) ................... 2010-195019

(51) Int. Cl.
*G01N 33/02*  (2006.01)
*G01N 3/40*  (2006.01)

(52) U.S. Cl.
CPC ............. *G01N 33/02* (2013.01); *G01N 3/405* (2013.01)

(58) Field of Classification Search
USPC ................. 73/661, 573, 579, 81, 78; 702/56
See application file for complete search history.

(56) References Cited

U.S. PATENT DOCUMENTS

| | | | | |
|---|---|---|---|---|
| 5,152,401 A | * | 10/1992 | Affeldt, Jr. ............. | G01N 3/405 209/556 |
| 5,691,473 A | * | 11/1997 | Peleg ....................... | G01N 3/32 209/599 |
| 6,276,536 B1 | * | 8/2001 | Terasaki ............... | G01N 29/045 209/556 |

(Continued)

FOREIGN PATENT DOCUMENTS

| | | |
|---|---|---|
| JP | 11-190688 | 7/1999 |
| JP | 2001-133374 | 5/2001 |

(Continued)

*Primary Examiner* — Paul West
*Assistant Examiner* — Xin Zhong
(74) *Attorney, Agent, or Firm* — K&L Gates LLP; Louis C. Cullman; Michelle Glasky Bergman

(57) ABSTRACT

In a vibration information detection step, a probe is inserted into a food sample, and any one of the displacement, the velocity or the acceleration of a vibration occurring on the probe by the insertion is detected as vibration information (step S1). In a frequency band dividing step, the vibration information is divided by a band pass filter into individual pieces of vibration information in each of a plurality of frequency bands (step S2). In a food texture index calculation step, a food texture index value based on vibrational energy per unit time in each of the frequency bands is calculated using a computer from the vibration information in each of the frequency bands and the center frequency of the corresponding frequency band (step S3).

16 Claims, 11 Drawing Sheets

(56) References Cited

U.S. PATENT DOCUMENTS

| | | | | |
|---|---|---|---|---|
| 6,539,781 B1* | 4/2003 | Crezee | ................. | G01N 3/405 |
| | | | | 73/573 |
| 2003/0216875 A1* | 11/2003 | Sakurai | ................. | G01N 29/12 |
| | | | | 702/56 |
| 2008/0092674 A1* | 4/2008 | Sakurai | ................. | G01N 3/405 |
| | | | | 73/866.5 |

FOREIGN PATENT DOCUMENTS

| JP | 2003-287524 | 10/2003 |
|---|---|---|
| JP | 2006-242892 | 9/2006 |
| JP | 2007-057476 | 3/2007 |
| JP | 2007-225460 | 9/2007 |
| JP | P4280836 | 6/2009 |

* cited by examiner

TEXTURE INDICATION MEASURING METHOD AND MEASURING DEVICES

TECHNICAL FIELD

The present invention relates to a measurement method of food texture index value and a measuring apparatus therefor.

BACKGROUND ART

We make a judgment on our preference concerning foods or farm products based on many elements, such as taste, smell and color. Among various elements we rely on as the basis for our judgment on preference, food texture is an especially important element. Such a food texture derives from mechanical characteristics (primarily elasticity or viscosity) of a food. Consequently, by measuring the elasticity or viscosity of a food, it should become possible to quantify the food texture. For example, a material testing machine has been disclosed, which quantifies customarily used food textures, such as "stickiness" or "al dente", by measuring mechanical characteristics of a food for a test sample, such as noodle or pasta (for example, see Patent Literature 1). By the material testing machine, a test sample such as noodle is thrust by a plunger to a constant distance and the plunger is retreated to a point where a stress (resilient force) given by the test sample on the plunger becomes zero, to obtain a curve showing the relationship between the retreated distance and the thrust load. And from the area of the region formed by the curve the repulsion energy inherent to the test sample is calculated and the "stickiness" or "al dente" of the test sample is quantified.

Food texture is however not limited to "stickiness" or "al dente". For example, a "crisp" texture in masticating fresh cucumber or celery, or a "creamy" texture of a ripe pear stimulates our appetite greatly. Since such food textures cannot be expressed by mechanodynamic measurements, for example, by a conventional rheometer, they have been always evaluated solely by a sensory evaluation (a test depending on human sense).

Further, a system for quantifying a "crunchiness" of a dry and porous food, such as a cookie or a snack, namely crispness, has been also disclosed recently (for example, see Patent Literature 2). According to the system, a rupture curve is determined by measurements, a frequency analysis is conducted for the determined rupture curve to determine rupture energy in a predetermined frequency region, and the crispness is quantified by the rupture energy.

Further, a food texture measuring apparatus has been disclosed that quantifies food textures such as a "crisp feeling" of a food irrespective of the water content (for example, see Patent Literature 2). According to the food texture measuring apparatus a probe is inserted into a food at a predetermined velocity, from signals outputted from a piezoelectric element connected with the probe the peak number of pulses per unit time is calculated, and the food texture is determined quantitatively by the peak number of pulses.

Further, a food texture measurement method for quantifying a "crisp feeling" and a "crunchiness" of a food has been disclosed (for example, see Patent Literature 4). According to the food texture measurement method, a probe is inserted into a food at a predetermined velocity, signals of a plurality of frequency bands are extracted from signals outputted from a piezoelectric element connected with the probe, and the amplitude density per unit time of the signals of each frequency band is determined as an index of a food texture of the food.

CITATION LIST

Patent Literature

[PTL 1] Unexamined Japanese Patent Application Kokai Publication No. H11-190688
[PTL 2] Unexamined Japanese Patent Application Kokai Publication No. 2001-133374
[PTL 3] Japanese Patent No. 4280836
[PTL 4] Unexamined Japanese Patent Application Kokai Publication No. 2007-57476

SUMMARY OF INVENTION

Technical Problem

For evaluating food accurately by means of a sensory evaluation, a plurality of well-trained examiners are necessary. For commodities demanding sophisticated tastes, such as wine or tobacco, such skillful examiners have been educated. However for low-priced farm products such as celery and cucumber, such education of experts are not performed, and in general, as the need arises, non-expert examiners are recruited who carry out a food texture determination according to a predetermined sensory evaluation schedule. Consequently, the evaluation results vary greatly and usually examiners are not the same person from one sensory evaluation to the next, exact comparison between the past measurement results and the present measurement results is difficult.

Further, by the system described in Patent Literature 2, the measurement object is limited to a dry porous food with water content of less than a given percentage. In other words, if applied to a food containing high moisture such as cucumber or lettuce, significant correlation between the rupture curve and the food texture cannot be always obtained.

The peak number of pulses per unit time measured by the food texture measuring apparatus described in Patent Literature 3 can be used to some extent as an index for a food texture. However, a food texture felt during eating depends dominantly on the fracture energy of a food generated by intraoral mastication. Therefore, it is more desirable to use for quantification a food texture index that is correlated to such fracture energy of a food.

The amplitude density per unit time measured by the food texture measuring apparatus described in Patent Literature 4 can be also used as a food texture index. The index is, however, also not highly correlated to the fracture energy of a food generated by intraoral mastication.

Under such circumstances the present invention was implemented with an object to provide a measurement method of a food texture index value that can quantify more accurately a food texture and a measuring apparatus therefor.

Solution to Problem

To attain the object, a measurement method of food texture index value related to the first viewpoint of the present invention comprises:
a vibration information detection step, in which a probe is inserted into a food sample, and any one physical value out of either the displacement, the velocity or the acceleration of a vibration occurring on the probe by the insertion is detected as vibration information using a vibration information detection unit that outputs stably the physical value in a predetermined frequency band;

a frequency band dividing step, in which the vibration information is divided by a band pass filter into individual pieces of vibration information in each of a plurality of frequency bands; and a food texture index calculation step, in which a food texture index value based on vibrational energy per unit time in each of the frequency bands is calculated using a computer from the vibration information in each of the frequency bands and the center frequency of the corresponding frequency band.

While, it is preferable that:

in the event the displacement of a vibration is detected as the vibration information in the vibration information detection step, the sum total of the square of the product of the vibration information and the center frequency, divided by unit time is calculated as vibrational energy per unit time in the food texture index calculation step;

in the event the velocity of a vibration is detected as the vibration information in the vibration information detection step, the sum total of the squared value of the vibration information, divided by unit time is calculated as vibrational energy per unit time in the food texture index calculation step; and in the event the acceleration of a vibration is detected as the vibration information in the vibration information detection step, the sum total of the square of the quotient of the vibration information divided by the center frequency, divided by unit time is calculated as vibrational energy per unit time in the food texture index calculation step.

Further, in the food texture index calculation step a food texture index value based on vibrational energy of each frequency band may be multiplied by a correction factor increasing gradually from a low frequency range to a high frequency range.

Further, the vibration information detection unit is forced to vibrate, and any one physical value out of either the acceleration, the velocity or the displacement generated in the vibration information detection unit is detected by another detection unit as the vibration information and an output signal value outputted from the vibration information detection unit is measured, a calibration factor for converting the measured output signal value to the vibration information detected by the other detection unit is determined, and in the food texture index calculation step, the vibration information in each of the frequency bands is multiplied by the calibration factor, and then the vibrational energy may be calculated.

Further, in the vibration information detection step, for the vibration information detection unit, an acceleration pickup that stably outputs a signal corresponding to acceleration in the predetermined frequency band may be used to detect the vibration information.

Further, in the food texture index calculation step, a food texture index value based on vibrational energy per unit time in each of the frequency bands may be calculated using voltage values outputted from the acceleration pickup according to the following expression 1:

[Math. 1]

$$T_i = \alpha \times \log_{10}\left(\frac{\sum_j V_{i,j}^2}{t \times f_i^2}\right) \quad \text{Expression 1}$$

(wherein $T_i$ is a food texture index value in a predetermined frequency band i; $\alpha$ is an arbitrary constant; $V_{i,j}$ is a voltage value in a predetermined frequency band i and a predetermined sampling j; t is a measurement time; and $f_i$ is the center frequency in a predetermined frequency band i).

Further, in the food texture index calculation step, a food texture index value based on vibrational energy per unit time in each of the frequency bands may be calculated using voltage values outputted from the acceleration pickup according to the following expression 2:

[Math. 2]

$$PinkT_i = \alpha \times \log_{10}\left\{\frac{f_i}{f_1} \cdot \frac{\sum_j V_{i,j}^2}{t \times f_i^2}\right\} \quad \text{Expression 2}$$

(wherein $PinkT_i$ is a food texture index value in a predetermined frequency band i; $\alpha$ is an arbitrary constant; $V_{i,j}$ is a voltage value in a predetermined frequency band i and a predetermined sampling j; t is a measurement time; $f_i$ is the center frequency in a predetermined frequency band i; and $f_1$ is the center frequency in a lowest frequency band).

Further, in the food texture index calculation step, a food texture index value based on vibrational energy per unit time in each of the frequency bands may be calculated using voltage values outputted from the acceleration pickup according to the following expression 3:

[Math. 3]

$$PinkT_i^{cal} = \alpha \times \log_{10}\left\{\frac{f_i}{f_1} \cdot \frac{\sum_j (V_{i,j} \times c(f_i))^2}{t \times f_i^2}\right\} \quad \text{Expression 3}$$

(wherein $PinkT^{cal}_i$ is a food texture index value in a predetermined frequency band i; $\alpha$ is an arbitrary constant; $V_{i,j}$ is a voltage value in a predetermined frequency band i and a predetermined sampling j; t is a measurement time; $f_i$ is the center frequency in a predetermined frequency band i; $f_1$ is the center frequency in a lowest frequency band; and $c(f_i)$ is a calibration factor determined for each frequency band).

Further, in the food texture index calculation step, the calculated food texture index value may be displayed comparatively together with White noise, Pink noise and Brownian noise for each frequency band.

Further, in the food texture index calculation step, a food texture index value based on vibrational energy per unit time in each of the frequency bands may be calculated using voltage values outputted from the acceleration pickup according to the following expression 4:

[Math. 4]

$$TPC_p = \sum_k a_{p,k} \cdot PinkT_k \quad \text{Expression 4}$$

(in the expression 4, $a_{p,k}$ is a predetermined factor, and $PinkT_k$ is a provisional food texture index value for a predetermined frequency band k to be calculated by the following expression 5):

[Math. 5]

$$PinkT_k = \alpha \times \log_{10}\left\{\frac{f_k}{f_1} \cdot \frac{\sum_j V_{k,j}^2}{t \times f_k^2}\right\} \quad \text{Expression 5}$$

(in the expression 5, α is an arbitrary constant; $V_{k,j}$ is a voltage value in a predetermined frequency band k at a predetermined sampling j; t is a measurement time; $f_k$ is the center frequency in a predetermined frequency band k; and $f_1$ is the center frequency in a lowest frequency band).

Further, the factor may be an eigenvector group determined by a principal component analysis from a provisional food texture index value group calculated by the expression 5 from previous measurements with respect to a pre-selected food group.

A measuring apparatus for a food texture index value related to the second viewpoint of the present invention comprises:

a probe that is inserted into a food sample;
a driving apparatus that drives the probe;
a vibration information detection apparatus that detects stably any one physical value out of either the displacement, the velocity or the acceleration of a vibration occurring on the probe by the insertion of the probe into the food sample as vibration information in a predetermined frequency band; and
a calculation apparatus that divides the vibration information by a band pass filter into individual pieces of vibration information in each of a plurality of frequency bands; and calculates a food texture index value based on vibrational energy per unit time in each of the frequency bands from the vibration information in each of the frequency bands and the center frequency of the corresponding frequency band.

The vibration information detection apparatus may be an acceleration pickup.

Further, the calculation apparatus may calculate a food texture index value based on vibrational energy per unit time in each of the frequency bands according to the following expression 1:

[Math. 6]

$$T_i = \alpha \times \log_{10}\left(\frac{\sum_j V_{i,j}^2}{t \times f_i^2}\right) \quad \text{Expression 1}$$

(wherein Ti is a food texture index value in a predetermined frequency band i; α is an arbitrary constant; $V_{i,j}$ is a voltage value in a predetermined frequency band i and a predetermined sampling j; t is a measurement time; and $f_i$ is the center frequency in a predetermined frequency band i).

Further, the calculation apparatus may calculate a food texture index value based on vibrational energy per unit time in each of the frequency bands according to the following expression 2:

[Math. 7]

$$PinkT_i = \alpha \times \log_{10}\left\{\frac{f_i}{f_1} \cdot \frac{\sum_j V_{i,j}^2}{t \times f_i^2}\right\} \quad \text{Expression 2}$$

(wherein $PinkT_i$ is a food texture index value in a predetermined frequency band i; α is an arbitrary constant; $V_{i,j}$ is a voltage value in a predetermined frequency band i and a predetermined sampling j; t is a measurement time; $f_i$ is the center frequency in a predetermined frequency band i; and $f_1$ is the center frequency in a lowest frequency band).

Further, the calculation processing may calculate a food texture index value based on vibrational energy per unit time in each of the frequency bands according to the following expression 3:

[Math. 8]

$$PinkT_i^{cal} = \alpha \times \log_{10}\left\{\frac{f_i}{f_1} \cdot \frac{\sum_j (V_{i,j} \times c(f_i))^2}{t \times f_i^2}\right\} \quad \text{Expression 3}$$

(wherein $PinkT^{cal}_i$ is a food texture index value in a predetermined frequency band i; α is an arbitrary constant; $V_{i,j}$ is a voltage value in a predetermined frequency band i and a predetermined sampling j; t is a measurement time; $f_i$ is the center frequency in a predetermined frequency band i; $f_1$ is the center frequency in a lowest frequency band; and $c(f_i)$ is a calibration factor determined for each frequency band).

Advantageous Effects of Invention

By a measurement method of a food texture index value according to the present invention, any one physical value out of either the displacement, the velocity or the acceleration of a vibration occurring on a probe by the insertion of the probe into a food sample is detected stably irrespective of the vibration frequency as vibration information. Consequently, the fracture energy by occasion of intraoral mastication of a food can be calculated accurately based on the vibration in a plurality of frequency bands. As the result, a food texture can be quantified more accurately.

DESCRIPTION OF EMBODIMENT

Figure 1:
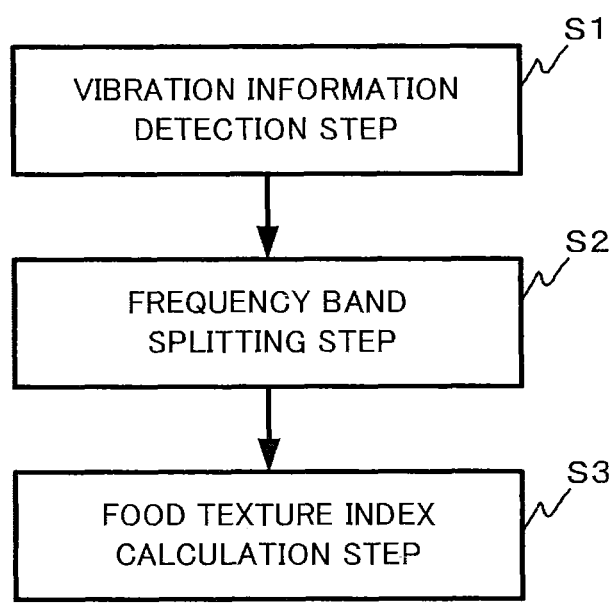
FIG. 1 is a flow diagram showing a measurement method of a food texture index value with respect to an embodiment of the present invention.

A measurement method of a food texture index value and a measuring apparatus of the food texture index value with respect to an embodiment of the present invention will be described below referring to the drawings. In FIG. 1 are shown steps of a measurement method of a food texture index value with respect to an embodiment of the present invention. As shown in FIG. 1 the measurement method of a food texture index value includes a vibration information detection step (step S1), a frequency band dividing step (step S2), and a food texture index calculation step (step S3).

Figure 2:
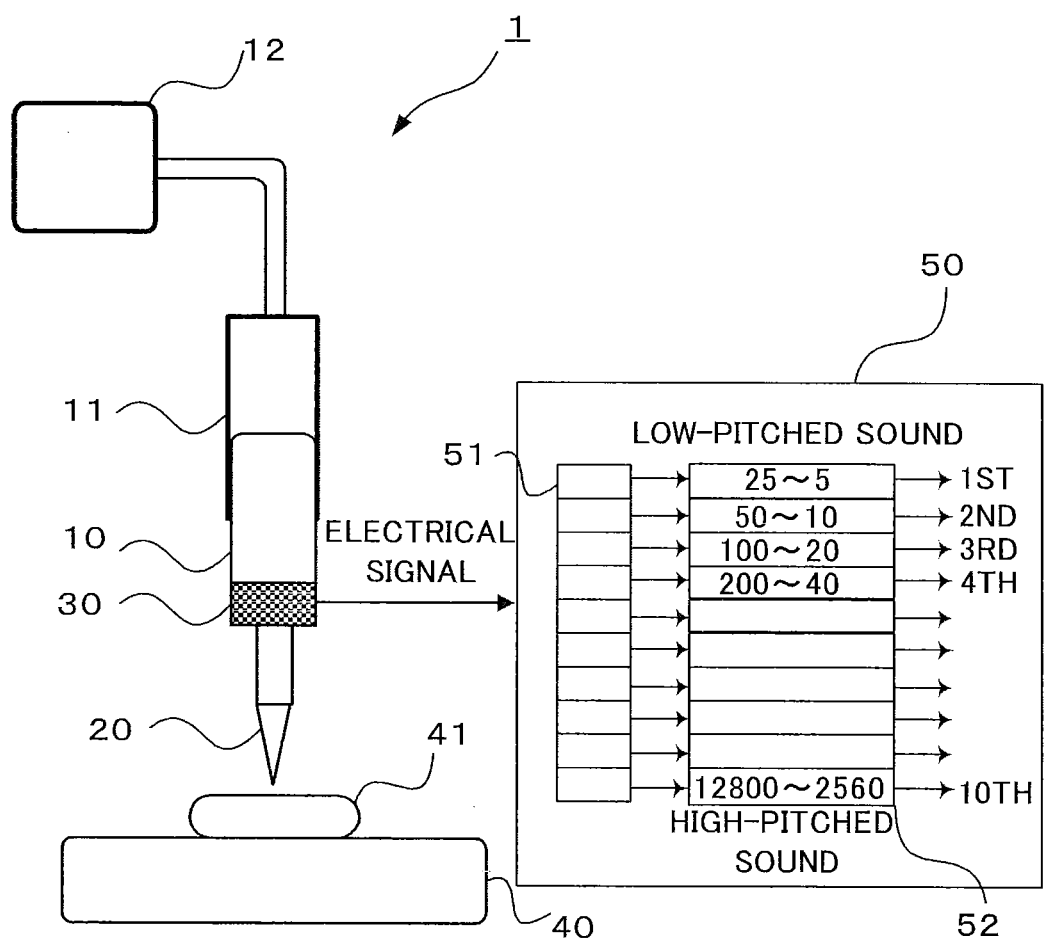
FIG. 2 is a schematic diagram of a structure of a measuring apparatus for a food texture index value with respect to an embodiment of the present invention.

In the vibration information detection step a probe (for example, probe 20 shown in FIG. 2) is inserted into a food sample (for example, food sample 41 shown in FIG. 2). While, any one physical value out of either the displacement, the velocity or the acceleration of a vibration occurring on the probe by the insertion of the probe into the food sample is detected as vibration information using a vibration information detection unit (for example, acceleration pickup 30) (step S1).

In the frequency band dividing step the vibration information is divided by a filter module (for example, filter module 51 shown in FIG. 2) as a band pass filter into individual pieces of vibration information in each of a plurality of frequency bands (step S2). The frequency band is preferably divided at intervals of an octave or half-octave as described below.

In the food texture index calculation step, a food texture index value based on vibrational energy per unit time in each of the frequency bands is calculated by a computer (for example, calculation apparatus 50 shown in FIG. 2) from the vibration information in each frequency band i and the center frequency of the corresponding frequency band (step S3). In this regard, the center frequency is the square root of the product of the minimum frequency and the maximum frequency of a predetermined frequency band i.

Energy is proportional to the square of velocity. Therefore, in the event the displacement of a vibration is detected as the vibration information in the vibration information detection step; in the food texture index calculation step, the product of the vibration information and the center frequency is found in each frequency band, and the sum total of the square of the product divided by unit time is determined as vibrational energy per unit time for each frequency band. While, in the event the velocity of a vibration is detected as the vibration information in the vibration information detection step; in the food texture index calculation step, the sum total of the squared value of the detected vibration information, divided by unit time is determined as vibrational energy per unit time for each frequency band. While, in the event the acceleration of a vibration is detected as the vibration information in the vibration information detection step; in the food texture index calculation step, the sum total of the square of the quotient of the vibration information divided by the center frequency, divided by unit time is determined as vibrational energy per unit time for each frequency band.

A measurement method of a food texture index value of the current embodiment is characterized in that a probe is inserted into a food sample, and any one physical value out of either the displacement, the velocity or the acceleration of a vibration occurring on the probe by the insertion is acquired as vibration information using a vibration detection unit. When a food texture is converted to vibrational energy, unless a physical value related to a vibration detected by a vibration detection unit is stably corresponding to any one out of the displacement, the velocity, and the acceleration of the vibration, accurate measurement of the vibrational energy is hardly possible. By the measurement method of a food texture index value of the current embodiment, a physical value, such as displacement of a vibration occurring on the probe, to be detected by a vibration detection unit (for example, acceleration pickup 30 shown in FIG. 2) is stable, for example, as a value corresponding to the acceleration, the fracture energy by occasion of intraoral mastication of a food can be measured accurately.

A food texture index value based on vibrational energy per unit time of each frequency band may be multiplied by a correction factor increasing gradually from a low frequency range to a high frequency range in the food texture index calculation step. By this action a food texture index based on vibrational energy in a high frequency range, which generally tends to attenuate faster, can be valued properly.

In order to correct the difference in food texture index values caused by different vibration information detection units used, the following operation should better be carried out, which will be described below taking an acceleration pickup as an example of a vibration information detection unit. Firstly, an acceleration pickup to be used is forced to vibrate, the displacement due to the vibration occurring on the acceleration pickup is detected by a laser Doppler meter, and the velocity and the acceleration of the body of the acceleration pickup are determined from the detected displacement. At the same time, the output signal value (voltage value) outputted from the acceleration pickup due to the forced vibration are measured. Plotting the acceleration according to the displacement detected by the laser Doppler meter and the output voltage values of the acceleration pickup on a graph, a linear relationship can be obtained. From the linear graph, a calibration factor for converting the output signal value (voltage value) to the acceleration is determined, and in an actual measurement, an output signal value converted by an acceleration pickup is multiplied with the predetermined calibration factor. Using such a calibration factor, a food texture index to be obtained may be deemed as a universal value. If the calibration factor values change with frequency, calibration factors different for each center frequency, namely for each frequency band may be multiplied.

A measurement method of a food texture index value of the current embodiment can be actualized, for example, with the measuring apparatus for a food texture index value shown in FIG. 2. A mode, in which an acceleration pickup 30 is used as a vibration information detection unit, and the acceleration as vibration information generated on a probe 20 is detected to determine a food texture index, will be described specifically below.

As shown in FIG. 2, a food texture index measuring apparatus 1 includes a plunger 10, a syringe 11, a pump 12, a probe 20, an acceleration pickup 30, a sample stage 40 and a calculation apparatus 50.

The pump 12 is a so-called oil-hydraulic pump containing inside a liquid such as oil. The pump 12 is connected through a transport tube with the syringe 11. The pump 12 is provided with an apparatus for changing the pressure to transport the liquid to the syringe 11. In this connection, an oil-hydraulic pump is used as the pump 12, because it does not cause unwanted vibration in inserting the probe 20 into a food sample 41, so that very accurate vibration signals can be detected.

The syringe 11 has inside a plunger 10. The internal space of the syringe 11 above the plunger 10 is fully filled with the liquid.

The plunger 10 is inserted contacting the inner wall of the syringe 11, and can move up and down according to the volume of the liquid in the syringe 11.

The probe 20 is mounted under the acceleration pickup 30. A tip of the probe 20 is inserted into the food. The tip of the probe 20 is designed to have a shape such that an appropriate vibration occurs by a contact with the food. Specific examples of the shape of the probe 20 may include cylindrical, prismatic, and the same with a tip pointed to form an acute angle. The probe 20 may be also conical. Further, the probe 20 may have a groove in addition to the above shape. As favorable examples of the probe 20 are conceivable a flat-blade screwdriver shape, and a flat-blade screwdriver shape with a groove.

The acceleration pickup 30 is placed between the plunger 10 and the probe 20. The acceleration pickup 30 is an element for converting detected vibrational energy to an electrical signal corresponding to the acceleration and outputting the same. Since the acceleration pickup 30 is in direct contact with the probe 20, the vibration occurring on the probe 20 is directly transmitted to the acceleration pickup 30. The acceleration pickup 30 is connected with the calculation apparatus 50 through a cable. The acceleration pickup 30 sends the output electrical signal (a voltage signal corresponding to the acceleration) through the cable to the calculation apparatus 50.

The sample stage 40 is a pedestal on which the food sample 41 is placed. The sample stage 40 is placed below the probe 20.

The calculation apparatus 50 has a filter module 51 and a calculation unit 52. The filter module 51 is band pass filters dividing an input electrical signal (output electrical signal of the acceleration pickup 30) to electrical signals having respective components of a plurality of frequency bands. The calculation unit 52 conducts arithmetic processing described in depth below to the electrical signal of each frequency band. The calculation apparatus 50 displays a measured voltage value and calculated results, and is provided with an interface with which further operation, arithmetic processing, or editing with respect to the displayed data is possible.

The food texture index measuring apparatus 1 to be used for a measurement method of a food texture index value of the current embodiment is characterized in that its vibration detection unit is configured to detect only one physical value out of the acceleration, the velocity, and the displacement.

Figure 3:
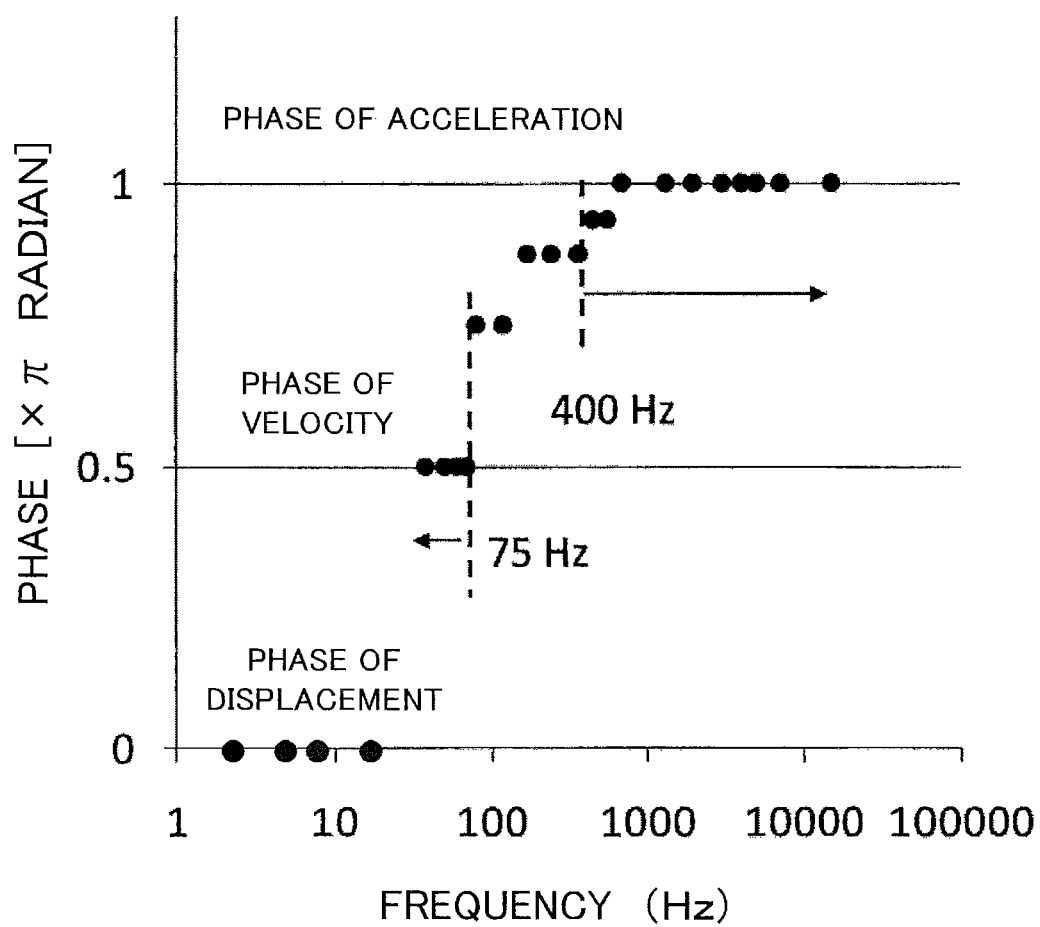
FIG. 3 is a graph showing a phase of a piezoelectric element sensor.

As this kind of a vibration detection unit a piezoelectric element instead of an acceleration pickup 30 has been heretofore used. FIG. 3 shows a relationship between the frequency and detection voltage, when a piezoelectric element is vibrated.

As shown in FIG. 3, in a frequency range from 2 Hz to about 10 Hz a piezoelectric element outputs voltage proportional to the displacement. For the frequency between about 10 Hz and about 100 Hz, it outputs voltage proportional to the velocity. While, the piezoelectric element outputs voltage proportional to the acceleration, if the frequency is above 400 Hz. While, the piezoelectric element outputs voltage proportional neither to the velocity nor the acceleration, if the frequency is 100 to 400 Hz. In other words, with a piezoelectric element, the correlation between a detected physical value and the output voltage is unstable depending on the vibration frequency.

Unless the relationship between a detected physical value and the output voltage of the vibration detection unit is constant, it becomes difficult to measure accurately vibrational energy based on the output voltage of the vibration detection unit. If a piezoelectric element is used, the relationship between the output voltage and a detected physical value is inconstant, and therefore it is not suitable for use as a vibration detection unit.

Figure 4:
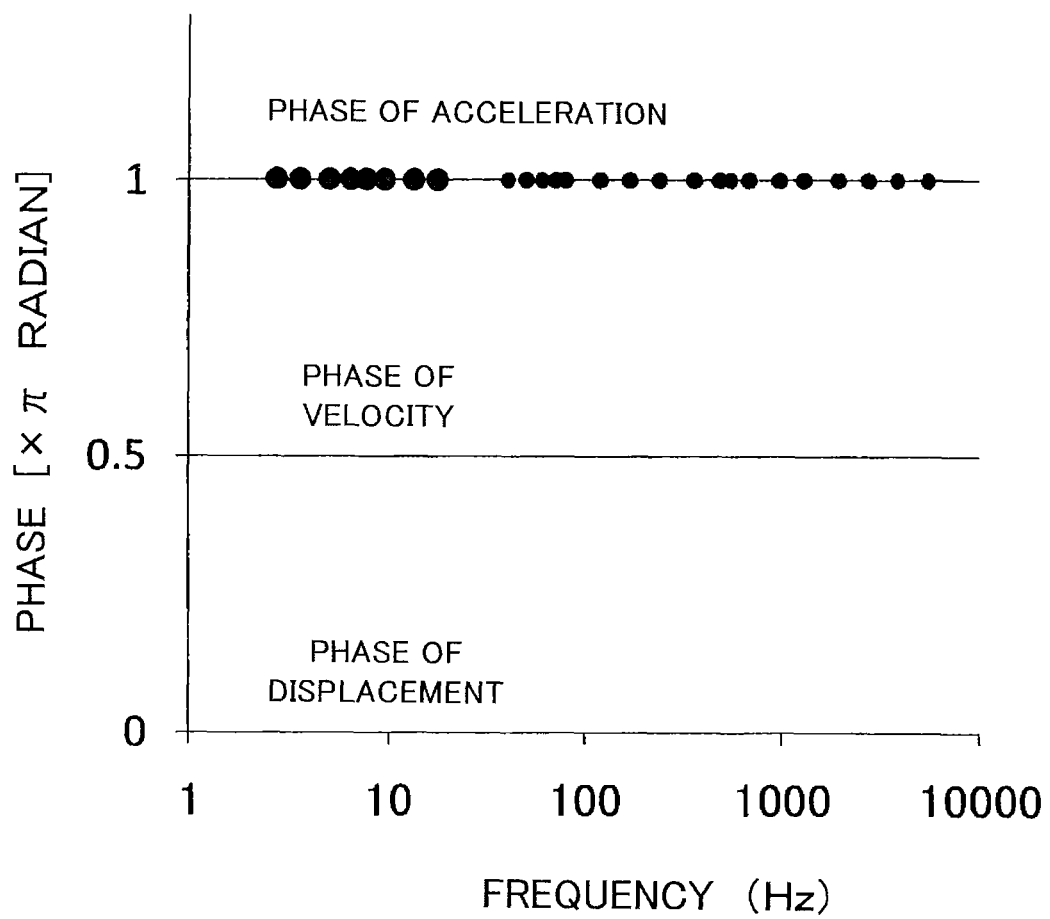
FIG. 4 is a graph showing a phase of an acceleration pickup.

Meanwhile, FIG. 4 shows the relationship between the frequency of a vibration raised by an acceleration pickup 30 (acceleration sensor) and the voltage detected by the acceleration pickup 30.

As shown in FIG. 4, the phase of the voltage outputted by the acceleration pickup 30 does not depend on the frequency and conforms with the phase of the acceleration. From this it is clear that the acceleration pickup 30 constantly outputs voltage proportional to the acceleration.

If a voltage proportional to a velocity is available, it has been known that the voltage can be converted to vibrational energy by squaring the voltage value. Reversely, it has been known that, if a voltage proportional to an acceleration is available, the voltage can be converted to vibrational energy by squaring the quotient of the voltage divided by the relevant center frequency. Consequently, when used as a vibration detection unit, an acceleration pickup 30 that outputs a voltage according to an acceleration, is used, an accurate measurement of vibrational energy is possible by detecting always the acceleration as a physical value by occasion of vibration irrespective of the vibration frequency.

The acceleration pickup 30 is provided with an adjustment circuit (not depicted) that adjusts the phase of a voltage signal outputted from a piezoelectric element connected with a pendulum to the phase of an acceleration. Owing to the adjustment circuit, the voltage signal outputted from the acceleration pickup 30 becomes a signal which constantly corresponds to the acceleration in a predetermined frequency band. Meanwhile, if the adjustment circuit adjusts the phase of a voltage signal outputted from a piezoelectric element to the phase of the displacement, the outputted voltage signal becomes a signal corresponds to the displacement. In this case, the vibration information detection unit becomes a displacement pickup. Further, if the adjustment circuit adjusts the phase of a voltage signal outputted from a piezoelectric element to the phase of the velocity, the outputted voltage signal becomes a signal corresponds to the velocity. In this case, the vibration information detection unit becomes a velocity pickup.

Next, measuring procedures for a food texture index value using the afore-described food texture index measuring apparatus 1 will be described.

Before a measurement a food sample 41 is placed on the sample stage 40. In this case the probe 20 should not touch the food sample 41.

Next a not-depicted switch of the measuring apparatus 1 is turned on to raise the liquid pressure of the pump 12. By the increase of the liquid pressure, the liquid in the pump 12 is transported into the syringe 11. Due to the increase of the liquid in the syringe 11, the plunger 10 descends. Corresponding to the decent of the plunger 10, the probe 20 descends toward the food sample 41.

After the tip of the probe 20 reaches the food sample 41, the probe 20 is further lowered and inserted into the food sample 41. By the pressure of the probe 20, the food sample 41 is fractured.

When the probe 20 is inserted in the food sample 41, the probe 12 touches cells and fibers of the food sample 41 or breaks them to cause a vibration of the probe 20. The occurred vibration is transmitted from the probe 20 to the acceleration pickup 30. The acceleration pickup 30 detects the acceleration of the vibration over the entire frequency region, and outputs electrical signals (voltage values) corresponding to the detected acceleration. The output voltage is transmitted through the cable to the calculation apparatus 50.

The voltage signal outputted from the acceleration pickup 30 and inputted to the calculation apparatus 50 is inputted to the filter module 51. The filter module 51 divides the inputted voltage signal to respective components for predetermined frequency bands.

For the calculation apparatus 50, the frequency band to be analyzed may be selected arbitrarily. Taking into consideration of the sensible upper limit of the frequency for human auditory sense, a preferable frequency band to be analyzed is, for example, a range of 0 to 25600 Hz. As for the sampling rate for the voltage signal, an arbitrary value, which is at least twice as high as the upper limit value of the analysis frequency range, is used. This is because according to the Nyquist principle sampling must be conducted at the frequency at least twice as high as the frequency subjected to analysis. Namely, to obtain information of 25600 Hz, measurements with the sampling rate not less than 51200 Hz are required.

For dividing the frequency range of 0 to 25600 Hz into a plurality of frequency bands, if octave filters are used as the filter module 51, the frequency band is divided as shown in the following table. The reason behind the dividing in octave units is based on the tendency that human sensory perception at high frequency is less sensible to increment compared to at low frequency.

TABLE 1

| OCTAVE FILTER | |
|---|---|
| BAND | FREQUENCY RANGE |
| 1 | 25~50 |
| 2 | 50~100 |
| 3 | 100~200 |
| 4 | 200~400 |
| 5 | 400~800 |
| 6 | 800~1600 |
| 7 | 1600~3200 |
| 8 | 3200~6400 |
| 9 | 6400~12800 |
| 10 | 12800~25600 |

If half-octave filters are used as the filter module 51, the frequency band is divided as shown in the following table. With the half-octave filters, the filtering treatment can be conducted with higher resolution than with the octave filters.

TABLE 2

| HALF-OCTAVE FILTER | |
|---|---|
| BAND | FREQUENCY RANGE |
| 1 | 25~35 |
| 2 | 35~50 |
| 3 | 50~71 |
| 4 | 71~100 |
| 5 | 100~141 |
| 6 | 141~200 |
| 7 | 200~283 |

TABLE 2-continued

| HALF-OCTAVE FILTER | |
|---|---|
| BAND | FREQUENCY RANGE |
| 8 | 283~400 |
| 9 | 400~566 |
| 10 | 566~800 |
| 11 | 800~1131 |
| 12 | 1131~1600 |
| 13 | 1600~2263 |
| 14 | 2263~3200 |
| 15 | 3200~4525 |
| 16 | 4525~6400 |
| 17 | 6400~9051 |
| 18 | 9051~12800 |
| 19 | 12800~18102 |
| 20 | 18102~25600 |

The calculation unit 52 calculates a food texture index value for each frequency band i based on electrical signals (voltage values) of each frequency band as divided above. According to the current embodiment electrical signals corresponding to the acceleration of an occurred vibration are obtained using the acceleration pickup 30, and the vibrational energy is calculated based on the electrical signals. As the result a food texture index value can be calculated based on the vibrational energy.

A computational expression derived from the above concept and used for arithmetic processing by the calculation unit 52 is shown below. The calculation unit 52 carries out a calculation using the expression 1 based on the electrical signals (voltage values) divided by the above method, to calculate a food texture index value.

[Math. 9]

$$T_i = \alpha \times \log_{10}\left(\frac{\sum_j V_{i,j}^2}{t \times f_i^2}\right) \quad \text{Expression 1}$$

In the above expression 1, $T_i$ is a food texture index value in a predetermined frequency band i, namely in each divided frequency band i. $\alpha$ is an arbitrary constant, for example 10. $V_{i,j}$ is a voltage value in a predetermined frequency band i and a predetermined sampling j. t is a measurement time in unit of second. $f_i$ is the center frequency in a predetermined frequency band i. The center frequency $f_i$ is the square root of the product of the minimum frequency and the maximum frequency of a predetermined frequency band. The entire frequency band to be analyzed is 0 to 25600 Hz. If the octave filters are used as the filter module 51 as shown in the above table, 10 food texture index values $T_i$ are calculated; and if the half-octave filters are used as the filter module 51, 20 food texture index values $T_i$ are calculated.

According to the expression 1 a food texture index value $T_i$ is calculated by integrating the square of voltage values $V_{i,j}$ over the measurement time and dividing the sum by the square of the center frequency and the measurement time. Therefore, a food texture index value $T_i$ is equivalent to the magnitude of the vibrational energy [$m^2/s^2$] received by the probe 20 per unit time. From an experiment using a laser Doppler meter, it is clear that a voltage value outputted by the acceleration pickup 30 depends on the acceleration in any frequency region. From the above, according to expression 1, a food texture index value $T_i$ is a logarithm of a value corresponding to the vibrational energy generated when the probe 20 is inserted into a food sample 41.

The calculation apparatus 50 displays graphically a food texture index value $T_i$ calculated for each frequency band. In this case a food texture index value $T_i$ calculated for each frequency band may be plotted as, for example, shown in FIG. 5 together with White noise, Pink noise, and Brownian noise. By introducing the divisions of White noise, Pink noise, and Brownian noise, evaluation of feelings of an eater with respect to the food texture of a food sample 41 subjected to the measurement can be facilitated.

In this regard, White noise means noise whose intensity of signal energy is uniform over the entire frequencies. While, Pink noise means noise whose intensity of signal energy is in inverse proportion to a frequency. Further, Brownian noise means noise whose intensity of signal energy is in inverse proportion to the square of a frequency.

In the field of acoustic engineering, the classification of White noise, Pink noise, Brownian noise is utilized in various analyses. There are many reports that as the results of noise analyses about sounds agreeable to the ear, Pink noise appears in them. For example, it is believed that people feel sounds of a waterfall or a stream agreeable, because they correspond to Pink noise. On the other hand, White noise is considered to give sounds unpleasant to the ear, and Brownian noise to give sounds with a feel that something is missing.

As described in the example below, by plotting food texture index values of a food sample 41 together with White noise, Pink noise, and Brownian noise for a graphical display, it becomes possible to judge, to which of White noise, Pink noise, or Brownian noise, the food texture index value close is. If, for example, the measured food texture index value of a food sample 41 is close to Pink noise, it is possible to judge that the food sample 41 will give, when eaten, an agreeable food texture. While, if it is close to White noise, a judgment of a rigid food texture, or if it is close to Brownian noise, a judgment of a food texture missing something is possible.

For putting Pink noise in the center to facilitate evaluation, the calculation unit 52 may carry out arithmetic processing using the expression 2 instead of the expression 1.

[Math. 10]

$$PinkT_i = \alpha \times \log_{10}\left\{\frac{f_i}{f_1} \cdot \frac{\sum_j V_{i,j}^2}{t \times f_i^2}\right\} \quad \text{Expression 2}$$

In the expression 2, $f_1$ is the center frequency in the lowest frequency band. Other items in the expression 2 are similar to those in the expression 1 and therefore further explanations are withheld.

A food texture index value $PinkT_i$ calculated according to the expression 2 is a food texture index value as a difference from a Pink noise. The Pink noise used as the reference for taking the difference is an absolute value with respect to $f_1$. By calculating a food texture index value $PinkT_i$ using the Pink noise as the reference, the discrepancy from sounds agreeable to the ear can be quantified.

As described in the Example below, by plotting the calculated food texture index value $PinkT_i$ for each frequency band together with the White noise, the Pink noise, and the Brownian noise, the difference of the obtained food texture index values of a food sample 41 from the Pink noise can be grasped at a glance. As the result, it can be instantly judged, in which frequency band the index agrees to the Pink noise and in which frequency band it differs how much from the Pink noise.

Since the food texture index value obtained as above is an absolute value based on the magnitude of vibrational energy, for comparing food textures between different apparatus the calculation unit 52 should better carry out arithmetic processing according to the expression 3 instead of the expression 1 or the expression 2.

[Math. 11]

$$PinkT_i^{cal} = \alpha \times \log_{10}\left\{\frac{f_i}{f_1} \cdot \frac{\sum_j (V_{i,j} \times c(f_i))^2}{t \times f_i^2}\right\} \quad \text{Expression 3}$$

In the expression 3, $c(f_i)$ is a calibration factor predetermined for each frequency band. Other items in the expression 3 are similar to those in the expressions 1 and 2 and therefore further explanations are withheld.

Since the food texture index value obtained as above is an absolute value, by plotting the absolute values obtained from different apparatus as described in the example below relative evaluation of a food texture can be conducted easier. Consequently, it can be easily judged from measurements of various foods using different apparatus, in which frequency band food texture index values coincide or do not, and can be clearly understood what features of a food texture such various foods have.

The food texture index values obtained by the above methods are calculated for a single food as many as the number of the filter modules 51, and an independent food texture index value is given for each frequency band and for each food. Therefore by applying a principal component analysis, which is one of analysis methods for a value group consisting of multivariables, a new calculation method of a food texture index value expressing more concisely a food texture can be provided. In the following paragraphs, a calculation method of a food texture index value utilizing a principal component analysis will be described.

A group of sample foods are selected appropriately. A measurement of a food texture index value is carried out for each of the selected group of sample foods using the food texture index measuring apparatus 1. In this regard, the calculation unit 52 finds $PinkT_k$, which is used as a provisional food texture index value, according to the expression 5 as a calculation expression for a food texture index.

[Math. 12]

$$PinkT_k = \alpha \times \log_{10}\left\{\frac{f_k}{f_1} \cdot \frac{\sum_j V_{k,j}^2}{t \times f_k^2}\right\} \quad \text{Expression 5}$$

If a group of sample foods consisting of M kinds of foods are measured and if the number of filter modules 51 is K, MxK provisional food texture index values are obtained. The calculation unit 52 carries out a principal component analysis on the MxK data to obtain an eigenvector. The relationship among them is shown in the following table.

TABLE 3

|  | | Filter k (1 ≤ k ≤ N) | | | | |
|---|---|---|---|---|---|---|
|  |  | 1 | 2 | 3 | 4 | ... K |
| Provisional food texture index values $PinkT_k$ for food sample m (1 · m · M) | 1 | $x_{11}$ | $x_{12}$ | $x_{13}$ | $x_{14}$ | ... $x_{1K}$ |
|  | 2 | $x_{21}$ | $x_{22}$ | $x_{23}$ | $x_{24}$ | ... $x_{2K}$ |
|  | 3 | $x_{31}$ | $x_{32}$ | $x_{33}$ | $x_{34}$ | ... $x_{3K}$ |
|  | ... | ... | ... | ... | ... | ... |
|  | M | $x_{M1}$ | $x_{M2}$ | $x_{M3}$ | $x_{M4}$ | ... $x_{MK}$ |
| 1st principal component eigenvector |  | $a_{11}$ | $a_{12}$ | $a_{13}$ | $a_{14}$ | ... $a_{1K}$ |
| 2nd principal component eigenvector |  | $a_{21}$ | $a_{22}$ | $a_{23}$ | $a_{24}$ | ... $a_{2K}$ |
| ... |  | ... | ... | ... | ... | ... |
| P-th principal component eigenvector |  | $a_{P1}$ | $a_{P2}$ | $a_{P3}$ | $a_{P4}$ | ... $a_{PK}$ |

$x_{mk}$ in Table 3 is a provisional food texture index value of the m-th (m=1 to M) food sample related to the k-th (k=1 to K) filter. While, $a_{pk}$ is the k-th element of the p-th principal component eigenvector. P is the number of the obtained eigenvectors. The 1st principal component through the P-th principal components are not mutually correlated variables, and examples thereof include the latitude of the production site of a food and a cooking temperature. The above procedure is conducted prior to the final measurement of a food, and a coefficient table ($a_{pk}$) consisting of the obtained eigenvectors is saved in the calculation apparatus 50.

Next a method for calculating a food texture index value $TPC_p$ of a food measured newly by a final measurement will be described. A food is measured newly, and for the provisional food texture index value $PinkT_k$ calculated according to the above expression 5, an inner product with the principal component eigenvectors in Table 3 is calculated according to the expression 4 (Expression 4).

[Math. 13]

$$TPC_p = \sum_k a_{p,k} \cdot PinkT_k \quad \text{Expression 4}$$

Thus, from P eigenvectors, P new food texture index values $TPC_p$ are calculated. Since the method is based on a principal component analysis, it is possible to select more important food texture index values out of the P obtained food texture index values $TPC_p$ as representative food texture index values. Further, if characteristic coefficients $a_{p,k}$ for each principal component can be narrowed down to some extent, the inner product of a provisional food texture index value $PinkT_k$ and specific limited coefficients $a_{p,k}$ corresponding to a filter k may be calculated. By doing so, compared to a food texture index value calculated according to any of the expression 1 to expression 3, the amount of information required for expressing a food texture can be reduced. In other words by calculating a food texture index value according to the expression 4, a food texture can be expressed more concisely.

Although a mode, in which an acceleration pickup 30 is used as the vibration information detection unit, and the acceleration pickup 30 detects the acceleration of a vibration occurring on a probe 20, is described in the above, the detection is not limited to the acceleration of a vibration. Since there is a convertible relationship from acceleration to velocity by integration, and from velocity to displacement by integration respectively, by detecting as vibration information the velocity or the displacement appeared on the probe 20 instead of the acceleration a food texture index value can be obtained similarly. For converting the vibration information to energy, if the vibration information detection unit outputs a voltage signal proportional to the velocity, the conversion can be made by squaring the voltage value; and if it outputs a voltage signal proportional to the displacement, the conversion to energy can be made by squaring the product of the voltage and the center frequency. As an example of a unit that can detects the velocity or displacement appeared on the probe 20 besides the acceleration pickup 30, a laser Doppler meter can be named.

As described above in detail, according to the current embodiment, a probe 20 is inserted into a food sample 41, and the acceleration as a physical value of a vibration occurring on the probe 20 by the insertion is detected by an acceleration pickup 30 stably as vibration information not dependent on the frequency. Consequently, the fracture energy by occasion of intraoral mastication of a food can be calculated accurately in a plurality of frequency bands based on the vibration. As the result, a food texture can be more accurately quantified.

Since an acceleration pickup 30 that always outputs voltage signals corresponding to acceleration as a physical value in the current embodiment, a food texture of a food that makes no sound when masticated, such as cheese, bread, jelly, and agar, can be also quantified.

EXAMPLE

A measurement of a food texture index was conducted for potato chips using the food texture measuring apparatus 1.

As the probe 20 a flat-blade screwdriver model (wedge shape) was used.

As the filter module 51 half-octave filters were used and analyzed a range from 0 to 25600 Hz.

A piece of potato chip was mounted on the sample stage, which was then fractured by feeding oil from the pump 12 into the syringe 11 at a constant rate and lowering the plunger 10.

A wave form outputted to a personal computer as the calculation apparatus 50 was observed and data relevant to a rising movement of the plunger after the measurement were eliminated from the measurement values.

The calculation unit 52 in a personal computer as the calculation apparatus 50 carries out an operation using the expression 1. As the results, a food texture index value for each frequency band was obtained.

The calculation unit 52 used the expression 2 to obtain a food texture index value for each frequency band.

The measurements were conducted 12 times.

Figure 5:
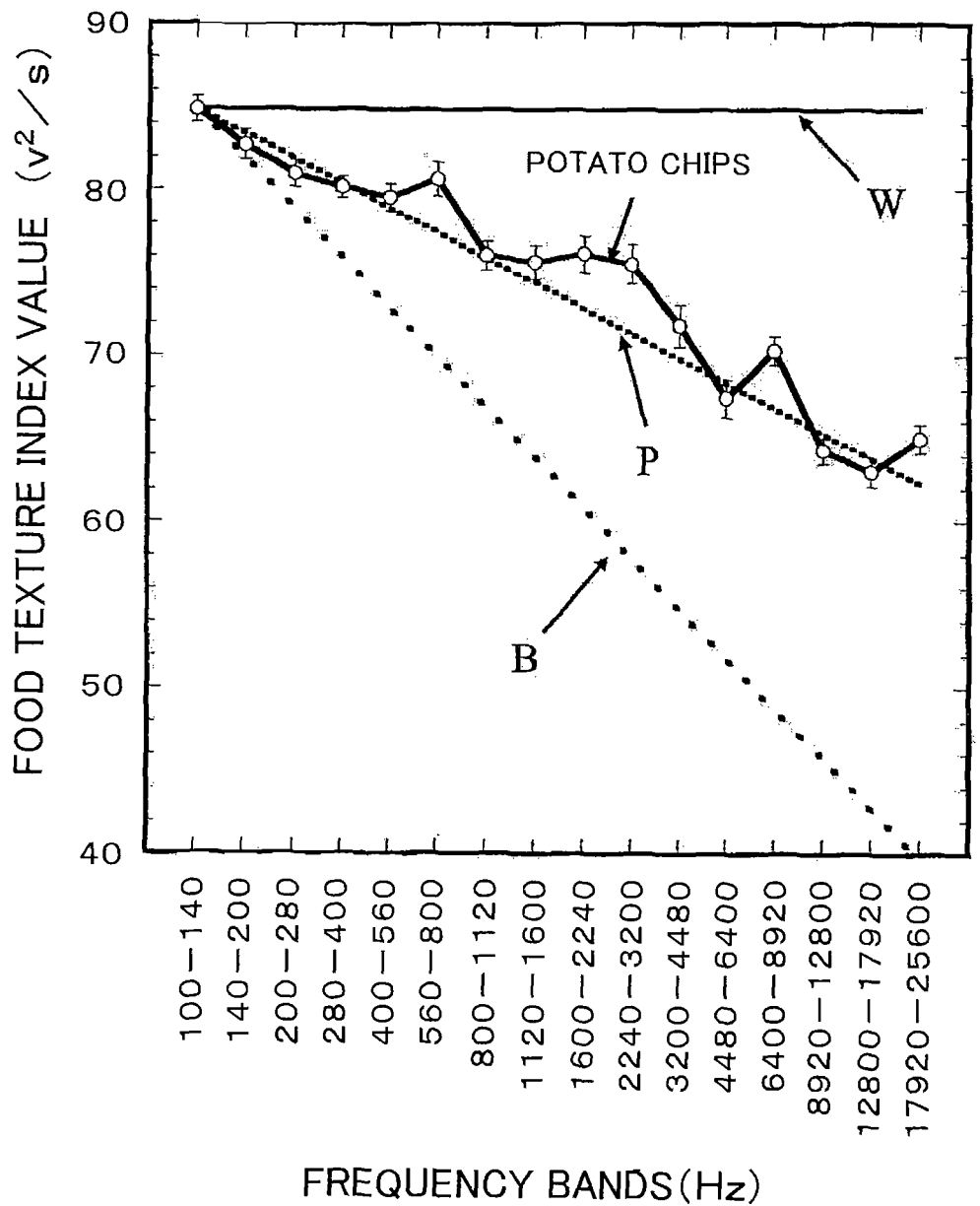
FIG. 5 is a graph showing a food texture index value for potato chips calculated by the expression 1.
Figure 6:
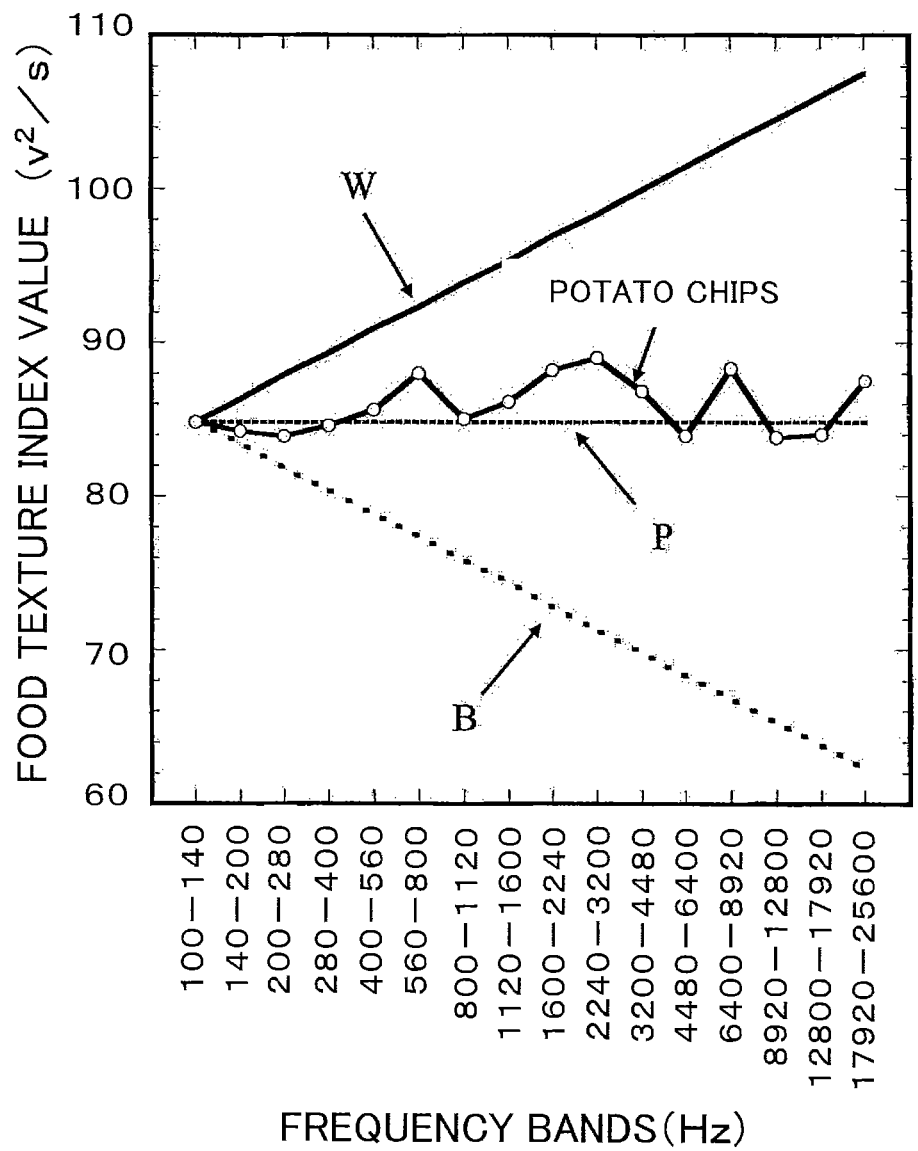
FIG. 6 is a graph showing a food texture index value for potato chips calculated by the expression 2.

The food texture index values obtained by using the expression 1, and the food texture index values obtained by using the expression 2 are shown in FIG. 5 and FIG. 6 respectively. In both the figures White noise (W), Pink noise (P) and Brownian noise (B) are also plotted.

In FIG. 5 and FIG. 6, in a low frequency range (100 to 560 Hz), frequency bands of 800 to 1120 Hz, 4480 to 6400 Hz, 8920 to 12800 Hz food texture index values close to the Pink noise are recognized. Meanwhile, in 560 to 800 Hz, 1600 to 3200 Hz, 6400 to 8920 Hz food texture index values are apparently closer to the White noise. Such food texture indices explain a crunchy food texture of potato chips.

Figure 7:
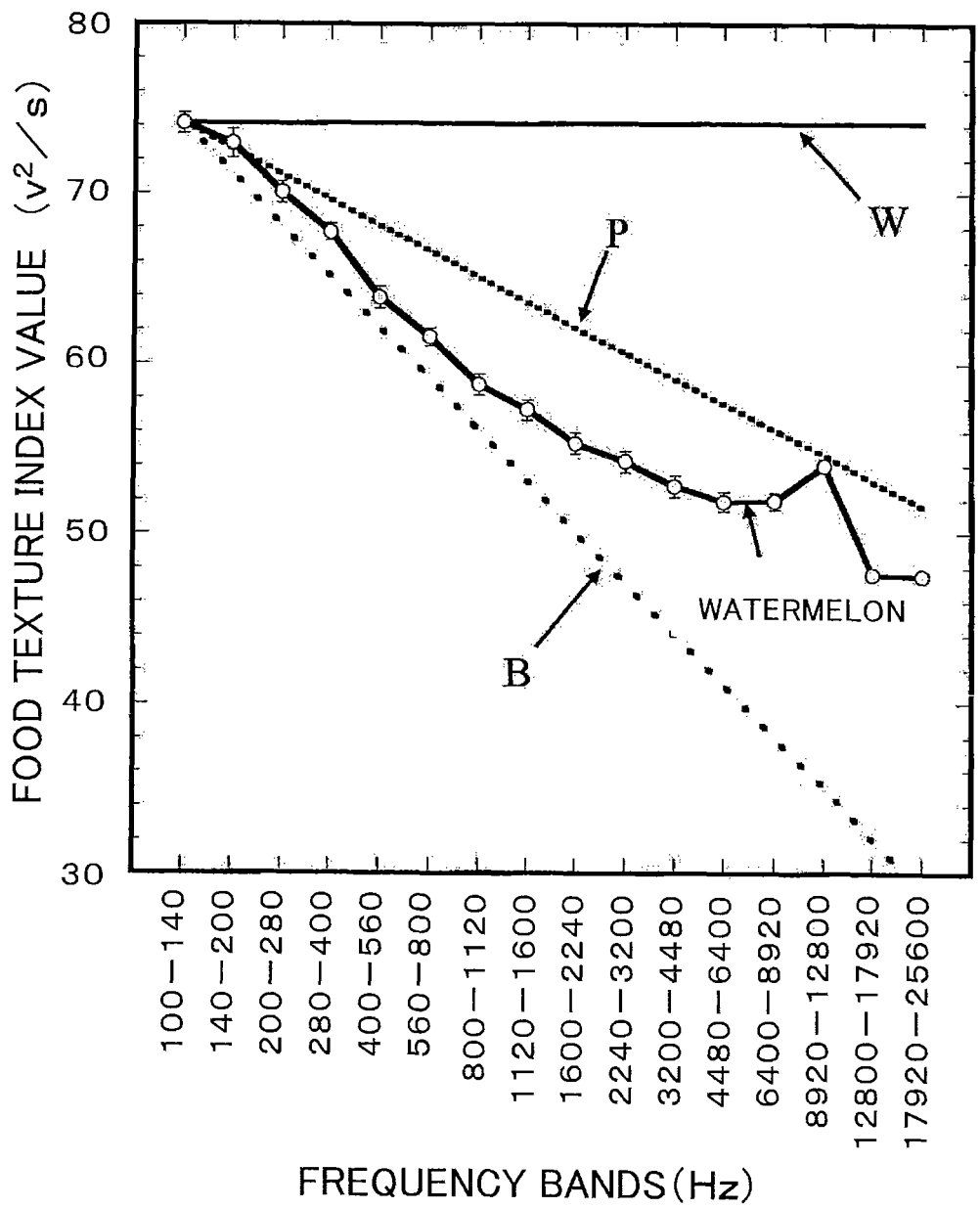
FIG. 7 is a graph showing a food texture index value for a watermelon calculated by the expression 1.
Figure 8:
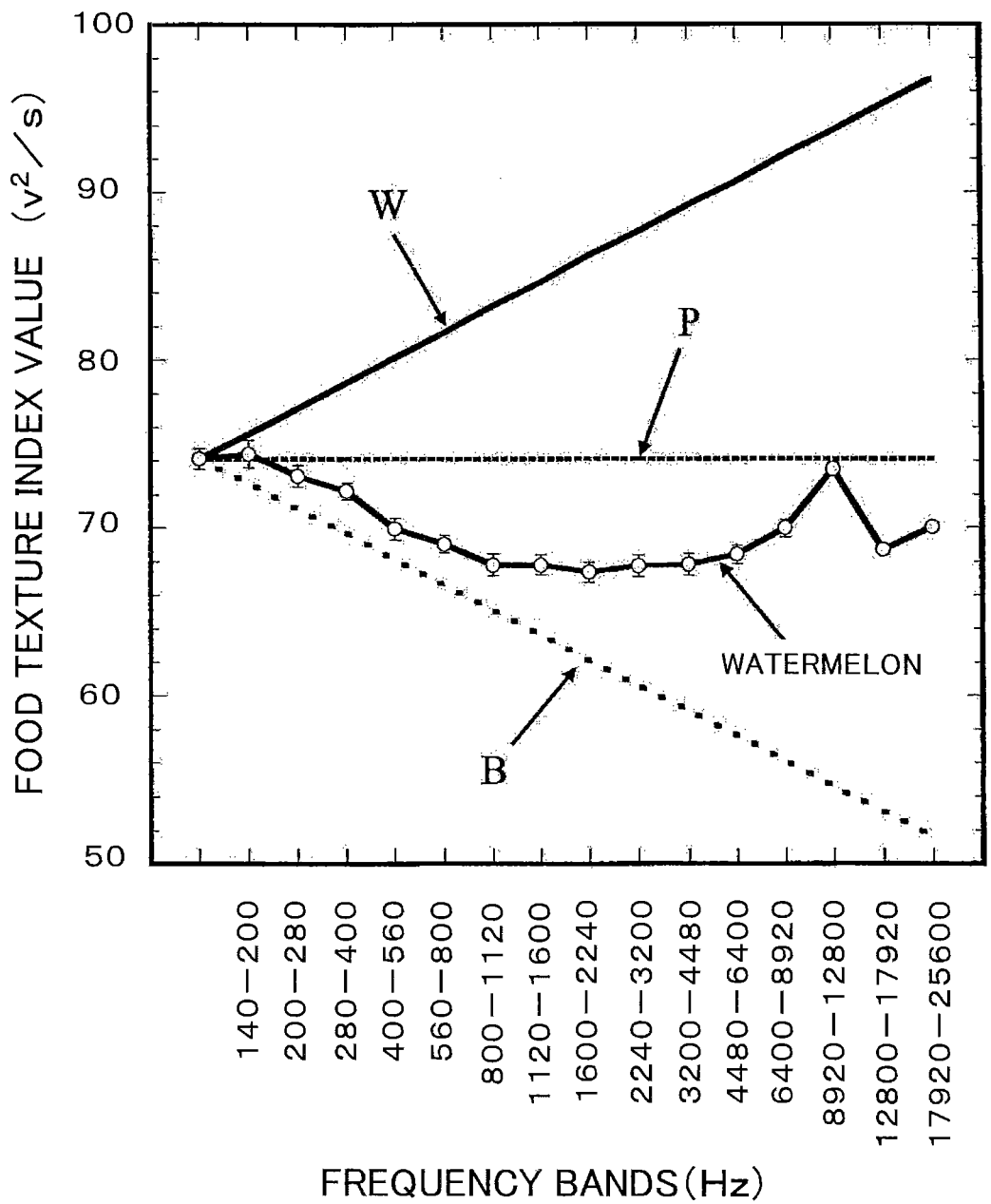
FIG. 8 is a graph showing food texture index value for a watermelon calculated by the expression 2.

Then, measurements of a food texture index value of a watermelon were carried out similarly as above. The results are shown in FIG. 7 and FIG. 8. The food texture index values obtained by using the expression 1, and the food texture index values obtained by using the expression 2 are shown in FIG. 7 and FIG. 8 respectively.

In FIG. 7 and FIG. 8, from 100 to 200 Hz a food texture index close to the Pink noise can be seen, but above 200 Hz a food texture index close to the Brownian noise, and above 4480 Hz again a food texture index close to the Pink noise can be seen. Such food texture indices explain a crisp food texture of a watermelon.

Figure 9:
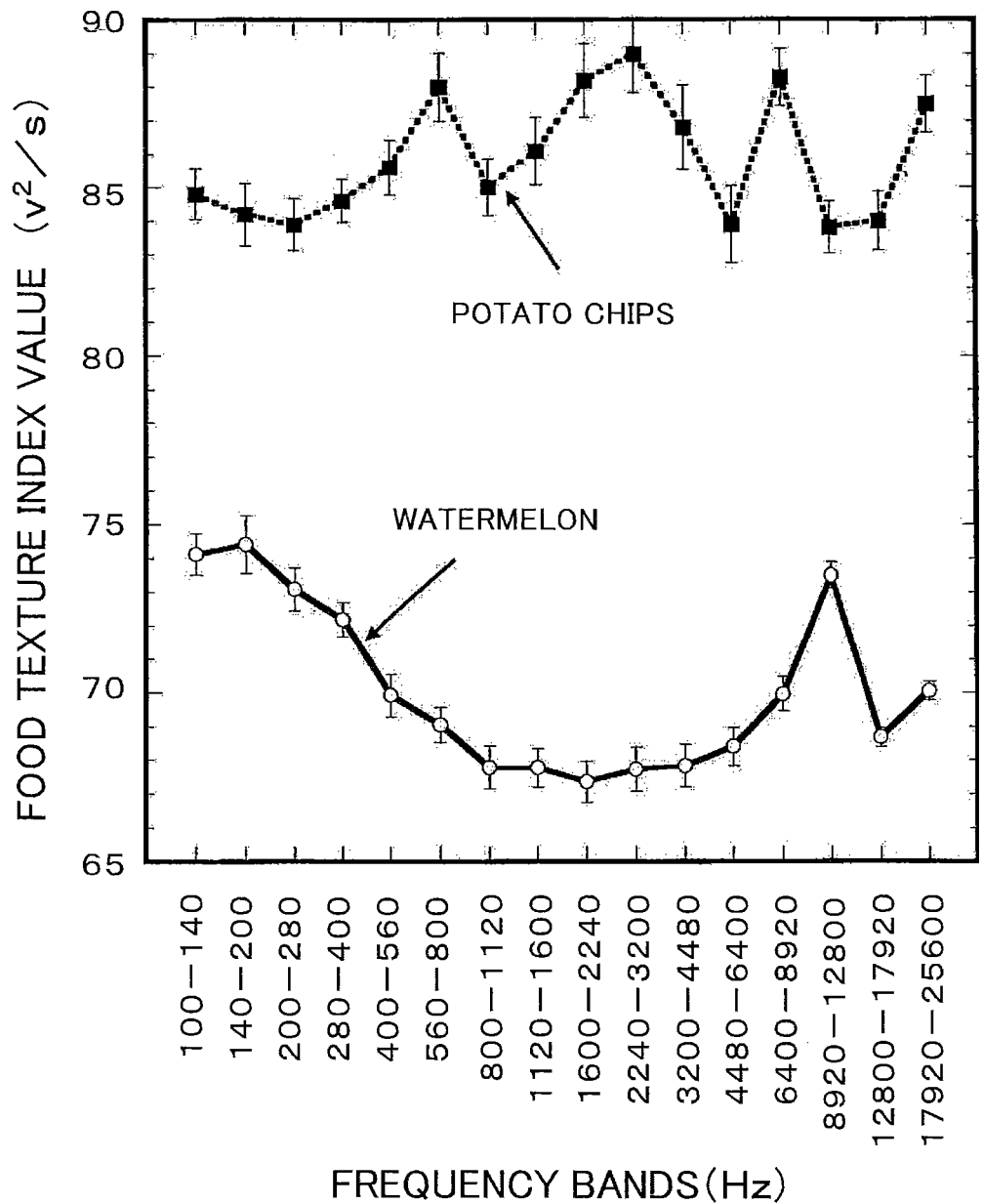
FIG. 9 is a graph showing food texture index values for potato chips and a watermelon calculated by the expression 2.

Food texture index values of potato chips and a watermelon obtained using the expression 2 are shown in FIG. 9. The absolute values of the food texture index values for potato chips are higher. This represents a chewier food texture of potato chips.

Figure 10:
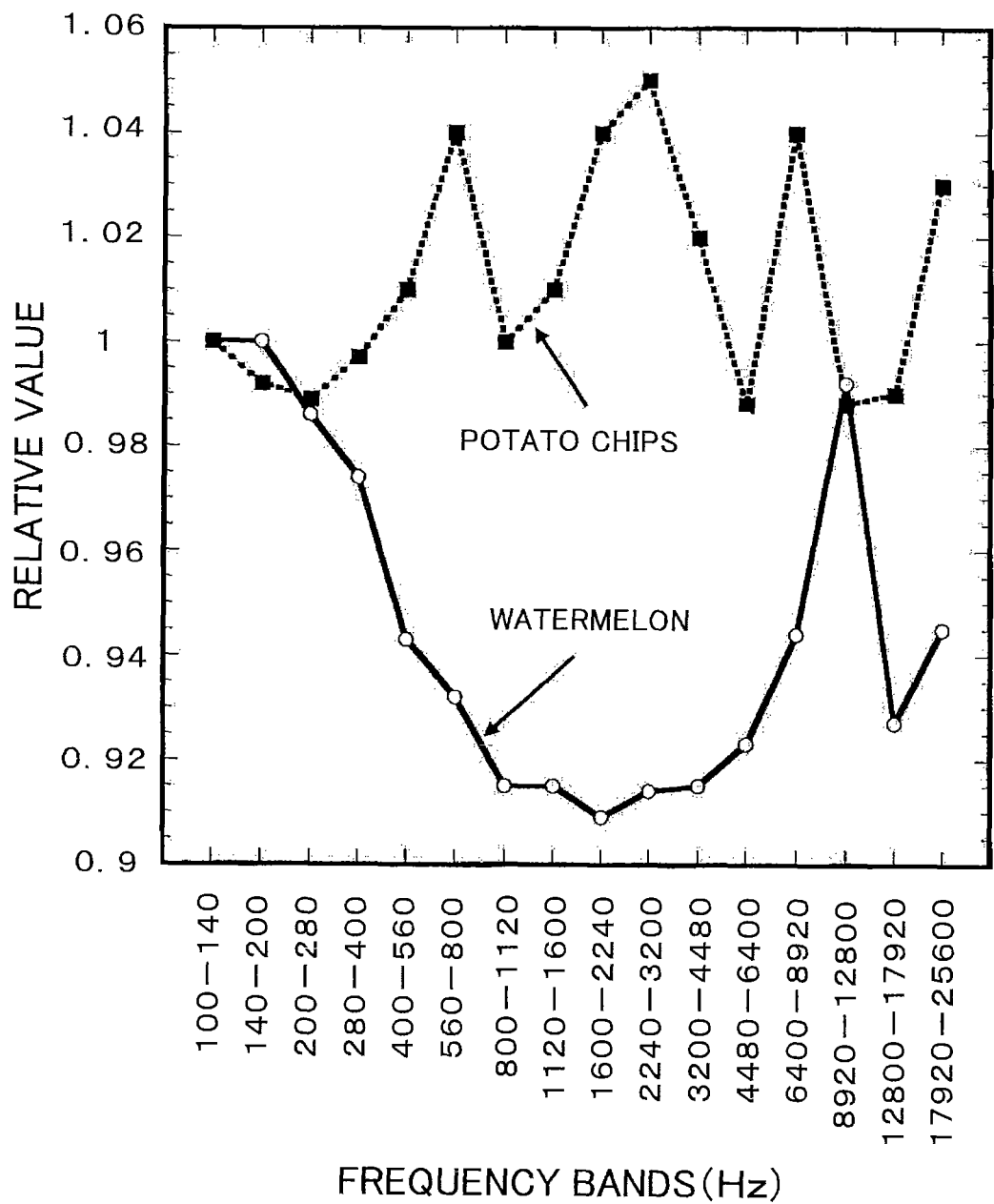
FIG. 10 is a graph showing food texture index values on potato chips and a watermelon calculated by the expression 3.

FIG. 10 shows food texture index values obtained by using the expression 3 for potato chips and a watermelon. In the case of a watermelon 280 to 8920 Hz contributes little as a food texture index value, but obviously food texture index values of 8920 to 12800 Hz are remarkably characteristic. In the case of potato chips, peaks of characteristic frequency bands are more clearly recognizable compared to a watermelon. Therefore as described above, by using the expression 3, features of different foods can be compared on the same graph.

Food texture index values measured by the food texture index measuring apparatus 1 of the current embodiment can not only quantify a difference between the food textures of foods having quite different qualities such as potato chips and a watermelon, but also indicate slight difference between food textures of similar foods. Food texture index values were measured for similar foods as follows, to detect a slighter difference in food textures.

Food texture index values were measured as above for 3 kinds of potato chips fried at different temperatures during cooking.

Figure 11:
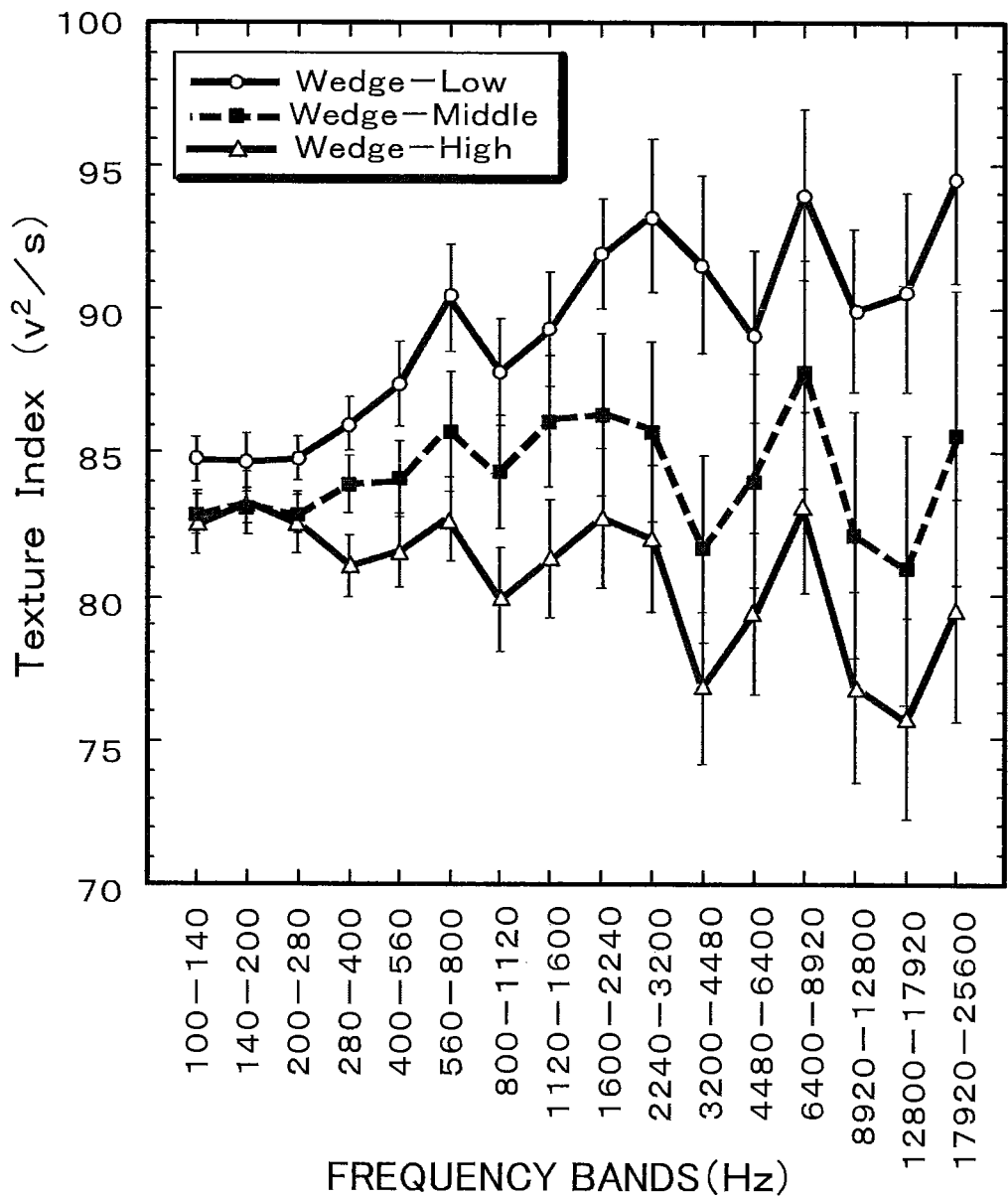
FIG. 11 is a graph showing food texture index values calculated by the expression 2 for potato chips fried at 3 kinds of different temperatures: a high temperature, an ordinary temperature and a low temperature.

FIG. 11 shows food texture index values for 3 kinds of potato chips fried at different temperatures of a high temperature, an ordinary temperature, and a low temperature. As obvious from FIG. 11, potato chips give different food textures depending on the frying temperature. Specifically, the food texture index value becomes larger in the order of potato chips fried at a high temperature (Wedge-High), potato chips fried at a middle temperature (Wedge-Middle), and potato chips fried at a low temperature (Wedge-Low). The results indicate that if potato chips fried at a lower temperature, the food texture becomes harder. Although the degree of the difference among them is slighter than the difference between the food texture index values of potato chips and a watermelon, it can be seen that such slight difference can be clearly quantified by the measuring apparatus of a food texture index value according to the current embodiment. Quantification of such a difference is useful for deciding an orientation to a preferable food texture in designing a food product, or a cooking method in actualizing the same.

With respect to the present invention various embodiments and modifications can be made without departing the spirit and scope thereof in the broad sense. The above embodiment is intended to be illustrative for easier understanding of the present invention but not to limit the scope of the invention. Namely, the scope of the present invention is not provided by the embodiment but by the claims. Therefore, changes and modifications made within the scope of the claims and within the scope of the spirit equivalent thereto are deemed as being within the scope of the present invention.

This application claims the benefit of priority to Japanese Patent Application No. 2010-195019, filed on 31 Aug., 2010.

The entire description, claims, and drawings of Japanese Patent Application No. 2010-195019 are hereby incorporated by reference.

INDUSTRIAL APPLICABILITY

A food texture index to be obtained by a food texture measurement method and a measuring apparatus according to the present invention can measure accurately vibrational energy appeared by occasion of insertion of a probe into a food. The index has therefore good reproducibility and is applicable to quality evaluations of various foods, or development of a food having a desired food texture index value by regulating a cooking method or source materials.

REFERENCE SIGNS LIST

1 Food texture index measuring apparatus
10 Plunger
11 Syringe
12 Pump
20 Probe
30 Acceleration pickup
40 Sample stage
41 Food sample
50 Calculation apparatus
51 Filter module
52 Calculation unit

What is claimed is:

1. A measurement method of a food texture index value comprising:
   a vibration information detection step, in which a probe is inserted into a food sample, and any one physical value out of either a displacement, a velocity or an acceleration of a vibration occurring on the probe during the insertion is detected as vibration information using a vibration information detection unit that outputs stably the physical value in a predetermined frequency band;
   a frequency band dividing step, in which the vibration information is divided by a band pass filter into individual pieces of vibration information in each of a plurality of frequency bands; and
   a food texture index calculation step, in which a food texture index value based on vibrational energy per unit time in each of the frequency bands is calculated using a computer from the vibration information in each of the frequency bands.

2. The measurement method of a food texture index value according to claim 1, wherein:
   in the event the displacement of a vibration is detected as the vibration information in the vibration information detection step,
   the sum total of the square of the product of the vibration information and a center frequency of the corresponding frequency band, divided by unit time is calculated as vibrational energy per unit time in the food texture index calculation step;
   in the event the velocity of a vibration is detected as the vibration information in the vibration information detection step,
   the sum total of the squared value of the vibration information, divided by unit time is calculated as vibrational energy per unit time in the food texture index calculation step; and
   in the event the acceleration of a vibration is detected as the vibration information in the vibration information detection step, the sum total of the square of the quotient of the vibration information divided by the center frequency, divided by unit time is calculated as vibrational energy per unit time in the food texture index calculation step.

3. The measurement method of a food texture index value according to claim 1, wherein a food texture index value based on vibrational energy of each frequency band is multiplied by a correction factor increasing gradually from a low frequency range to a high frequency range in the food texture index calculation step.

4. The measurement method of a food texture index value according to claim 1, wherein:
the vibration information detection unit is forced to vibrate, and any one physical value out of either the acceleration, the velocity or the displacement generated in the vibration information detection unit is detected by another detection unit as the vibration information and an output signal value outputted from the vibration information detection unit is measured,
a calibration factor for converting the measured output signal value to the vibration information detected by the other detection unit is determined, and
in the food texture index calculation step, the vibration information in each of the frequency bands is multiplied by the calibration factor, and then the vibrational energy is calculated.

5. The measurement method of a food texture index value according to claim 1, wherein:
in the vibration information detection step, using an acceleration pickup as the vibration information detection unit for outputting stably a signal corresponding to acceleration in the predetermined frequency band to detect the vibration information.

6. The measurement method of a food texture index value according to claim 5, wherein:
in the food texture index calculation step,
a food texture index value based on vibrational energy per unit time in each of the frequency bands is calculated using voltage values outputted from the acceleration pickup according to expression 1:

[Math. 1]

$$T_i = \alpha \times \log_{10}\left(\frac{\sum_j V_{i,j}^2}{t \times f_i^2}\right) \quad \text{Expression 1}$$

wherein $T_i$ is a food texture index value in a predetermined frequency band i; $\alpha$ is an arbitrary constant; $V_{i,j}$ is a voltage value in a predetermined frequency band i and a predetermined sampling j; t is a measurement time; and $f_i$ is the center frequency in a predetermined frequency band i.

7. The measurement method of a food texture index value according to claim 5, wherein:
in the food texture index calculation step,
a food texture index value based on vibrational energy per unit time in each of the frequency bands is calculated using voltage values outputted from the acceleration pickup according to expression 2:

[Math. 2]

$$PinkT_i = \alpha \times \log_{10}\left\{\frac{f_i}{f_1} \cdot \frac{\sum_j V_{i,j}^2}{t \times f_i^2}\right\} \quad \text{Expression 2}$$

wherein $PinkT_i$ is a food texture index value in a predetermined frequency band i; $\alpha$ is an arbitrary constant; $V_{i,j}$ is a voltage value in a predetermined frequency band i and a predetermined sampling j; t is a measurement time; $f_i$ is the center frequency in a predetermined frequency band i; and $f_1$ is the center frequency in a lowest frequency band.

8. The measurement method of a food texture index value according to claim 5, wherein:
in the food texture index calculation step,
a food texture index value based on vibrational energy per unit time in each of the frequency bands is calculated using voltage values outputted from the acceleration pickup according to expression 3:

[Math. 3]

$$PinkT_i^{cal} = \alpha \times \log_{10}\left\{\frac{f_i}{f_1} \cdot \frac{\sum_j (V_{i,j} \times c(f_i))^2}{t \times f_i^2}\right\} \quad \text{Expression 3}$$

wherein $PinkT^{cal}_i$ is a food texture index value in a predetermined frequency band i; $\alpha$ is an arbitrary constant; $V_{i,j}$ is a voltage value in a predetermined frequency band i and a predetermined sampling j; t is a measurement time; $f_i$ is the center frequency in a predetermined frequency band i; $f_1$ is the center frequency in a lowest frequency band; and $c(f_i)$ is a calibration factor determined for each frequency band.

9. The measurement method of a food texture index value according to claim 6, wherein:
in the food texture index calculation step,
the calculated food texture index value is displayed comparatively together with White noise, Pink noise and Brownian noise for each frequency band.

10. The measurement method of a food texture index value according to claim 5, wherein:
in the food texture index calculation step,
a food texture index value based on vibrational energy per unit time in each of the frequency bands is calculated using voltage values outputted from the acceleration pickup according to the following expression 4:

[Math. 4]

$$TPC_p = \sum_k a_{p,k} \cdot PinkT_k \quad \text{Expression 4}$$

wherein in the expression 4, $a_{p,k}$ is a predetermined factor, and $PinkT_k$ is a provisional food texture index value for a predetermined frequency band k to be calculated by expression 5:

[Math. 5]

$$PinkT_k = \alpha \times \log_{10}\left\{\frac{f_k}{f_1} \cdot \frac{\sum_j V_{k,j}^2}{t \times f_k^2}\right\} \quad \text{Expression 5}$$

wherein in the expression 5, $\alpha$ is an arbitrary constant; $V_{k,j}$ is a voltage value in a predetermined frequency band k at a predetermined sampling j; t is a measurement time; $f_k$ is the center frequency in a predetermined frequency band k; and $f_1$ is the center frequency in a lowest frequency band.

11. The measurement method of a food texture index value according to claim 10, wherein:
the factor is an eigenvector group determined by a principal component analysis from a provisional food texture index value group calculated by the expression 5 from previous measurements with respect to a preselected food group.

12. A measuring apparatus for a food texture index value comprising:
a probe that is inserted into a food sample;
a driving apparatus that drives the probe;
a vibration information detection apparatus that stably detects any one physical value out of either a displacement, a velocity or an acceleration of a vibration occurring on the probe by the insertion of the probe into the food sample as vibration information in a predetermined frequency band; and
a calculation apparatus that divides the vibration information by a band pass filter into individual pieces of vibration information in each of a plurality of frequency bands; and calculates a food texture index value based on vibrational energy per unit time in each of the frequency bands from the vibration information in each of the frequency bands.

13. The measuring apparatus for a food texture index value according to claim 12, wherein the vibration information detection apparatus is an acceleration pickup.

14. The measuring apparatus for a food texture index value according to claim 13, wherein:
the calculation apparatus calculates a food texture index value based on vibrational energy per unit time in each of the frequency bands according to expression 1:

[Math. 6]

$$T_i = \alpha \times \log_{10}\left(\frac{\sum_j V_{i,j}^2}{t \times f_i^2}\right) \quad \text{Expression 1}$$

wherein $T_i$ is a food texture index value in a predetermined frequency band i; $\alpha$ is an arbitrary constant; $V_{i,j}$ is a voltage value in a predetermined frequency band i and a predetermined sampling j; t is a measurement time; and $f_i$ is the center frequency in a predetermined frequency band i.

15. The measuring apparatus for a food texture index value according to claim 13, wherein:
the calculation apparatus calculates a food texture index value based on vibrational energy per unit time in each of the frequency bands according to expression 2:

[Math. 7]

$$PinkT_i = \alpha \times \log_{10}\left\{\frac{f_i}{f_1} \cdot \frac{\sum_j V_{i,j}^2}{t \times f_i^2}\right\} \quad \text{Expression 2}$$

wherein $PinkT_i$ is a food texture index value in a predetermined frequency band i; $\alpha$ is an arbitrary constant; $V_{i,j}$ is a voltage value in a predetermined frequency band i and a predetermined sampling j; t is a measurement time; $f_i$ is the center frequency in a predetermined frequency band i; and $f_1$ is the center frequency in a lowest frequency band.

16. The measuring apparatus for a food texture index value according to claim 13, wherein:
the calculation processing calculates a food texture index value based on vibrational energy per unit time in each of the frequency bands according to expression 3:

[Math. 8]

$$PinkT_i^{cal} = \alpha \times \log_{10}\left\{\frac{f_i}{f_1} \cdot \frac{\sum_j (V_{i,j} \times c(f_i))^2}{t \times f_i^2}\right\} \quad \text{Expression 3}$$

wherein $PinkT_i^{cal}$ is a food texture index value in a predetermined frequency band i; $\alpha$ is an arbitrary constant; $V_{i,j}$ is a voltage value in a predetermined frequency band i and a predetermined sampling j; t is a measurement time; $f_i$ is the center frequency in a predetermined frequency band i; $f_1$ is the center frequency in a lowest frequency band; and $c(f_i)$ is a calibration factor determined for each frequency band.

\* \* \* \* \*